(12) United States Patent
Van Eis et al.

(10) Patent No.: US 7,851,475 B2
(45) Date of Patent: Dec. 14, 2010

(54) SUBSTITUTED PYRROLE-2, 5-DIONES AS PROTEIN KINASE C INHIBITORS

(75) Inventors: Maurice Van Eis, St. Louis (FR); Jürgen Wagner, Bottmingen (CH); Peter Von Matt, Biel-Benken BL (CH)

(73) Assignee: Novartis AG, Basel (CH)

( * ) Notice: Subject to any disclaimer, the term of this patent is extended or adjusted under 35 U.S.C. 154(b) by 1092 days.

(21) Appl. No.: 11/568,055

(22) PCT Filed: May 12, 2005

(86) PCT No.: PCT/EP2005/005183

§ 371 (c)(1),
(2), (4) Date: Oct. 18, 2006

(87) PCT Pub. No.: WO2005/113545

PCT Pub. Date: Dec. 1, 2005

(65) Prior Publication Data

US 2009/0221605 A1    Sep. 3, 2009

(30) Foreign Application Priority Data

May 13, 2004   (GB) ................... 0410713.2

(51) Int. Cl.
*A61K 31/497* (2006.01)
*A61K 31/50* (2006.01)
*A61K 31/501* (2006.01)
*A61K 31/517* (2006.01)
*A01N 43/54* (2006.01)
*C07D 403/00* (2006.01)

(52) U.S. Cl. ............... 514/254.09; 544/373; 514/252.1; 514/266.2

(58) Field of Classification Search ............ 514/254.09, 514/252.1, 266.2; 544/373
See application file for complete search history.

(56) References Cited

U.S. PATENT DOCUMENTS

2003/0069424 A1 *   4/2003   Albert et al. ................. 544/284

FOREIGN PATENT DOCUMENTS

| WO | 02/38561 | 5/2002 |
| WO | 03/082859 | 10/2003 |

* cited by examiner

*Primary Examiner*—Sreeni Padmanabhan
*Assistant Examiner*—Umamaheswari Ramachandran
(74) *Attorney, Agent, or Firm*—Hoxie & Associates LLC

(57) ABSTRACT

A compound of formula I

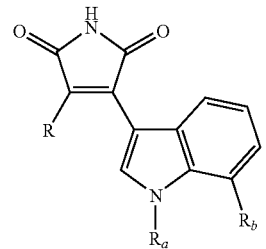

wherein R, $R_a$ and $R_b$ are as defined in the specification, processes for their production, their uses, in particular in transplantation, and pharmaceutical compositions containing them.

5 Claims, No Drawings

SUBSTITUTED PYRROLE-2, 5-DIONES AS PROTEIN KINASE C INHIBITORS

The present invention relates to indolylmaleimide derivatives, process for their production and pharmaceutical compositions containing them.

More particularly the present invention provides a compound of formula I

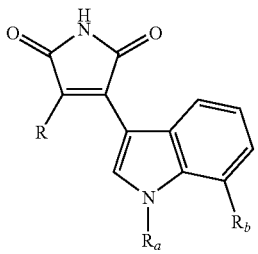

I wherein $R_a$ is H; $C_{1-4}$alkyl; or $C_{1-4}$alkyl substituted by OH, $NH_2$, $NHC_{1-4}$alkyl or $N(C_{1-4}alkyl)_2$;

$R_b$ is H; halogen; $C_{1-6}$alkyl; or $C_{1-6}$alkoxy, and

R is a radical of formula (a)

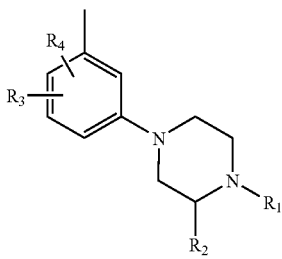

(a)

wherein each of $R_1$ and $R_2$, independently, is H or methyl;

$R_3$ is F, Cl, acetamide, nitro or amino;

$R_4$ is H, $CH_3$, $CF_3$, F, or Cl; $R_4$ being other than H, $CH_3$ or $CF_3$ when $R_3$ is Cl.

In the compounds of formula I, the following significances are preferred individually or in any sub-combination:

1. $R_a$ is H or methyl;
2. $R_b$ is H, methyl or ethyl;
3. $R_1$ is methyl;
4. $R_2$ is H;
5. $R_3$ is F, Cl or nitro;
6. $R_3$ is attached in position 2;
7. $R_4$ is H or F wherein $R_4$ is other than H when $R_3$ is Cl;
8. $R_4$ is attached in position 4.

The compounds of formula I may exist in free form or in salt form, e.g. addition salts with e.g. organic or inorganic acids, for example, hydrochloric acid, acetic acid or trifluoroacetic acid.

It will be appreciated that the compounds of formula I may exist in the form of optical isomers, racemates or diastereoisomers. For example, a ring carbon atom bearing a substituent in the position 3 of the piperazinyl residue is asymmetric and may have the D- or L-configuration. It is to be understood that the present invention embraces all enantiomers and their mixtures. Similar considerations apply in relation to starting materials exhibiting asymmetric carbon atoms as mentioned.

The present invention also includes a process for the preparation of a compound of formula I which process comprises reacting a compound of formula II

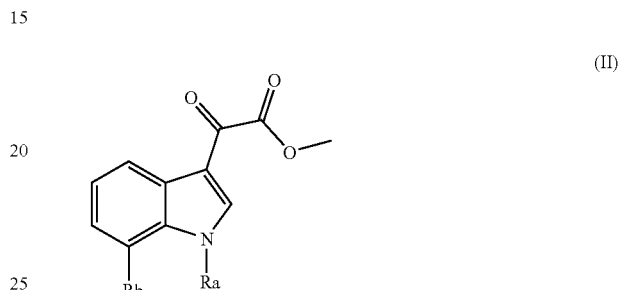

(II)

wherein $R_a$ and $R_b$ are as defined above, with a compound of formula III $$R-CH_2-CO-NH_2 \quad (III)$$

wherein R is as defined above, and, where required, converting the resulting compound of formula I obtained in free form to a salt form or vice versa, as appropriate.

The process may conveniently be effected in the presence of a strong base, e.g. t-BuOK, e.g. as disclosed in WO 02/38561.

Compounds of formula II and III may be prepared in accordance with known methods, e.g. as disclosed in WO 02/38561 and WO 03/082859.

Insofar as the production of the starting materials is not particularly described, the compounds are known or may be prepared analogously to methods known in the art or as described hereafter.

The following examples are illustrative of the invention.

| | |
|---|---|
| RT = | room temperature |
| DMF = | dimethylformamide |
| THF = | tetrahydrofuran |
| FCC = | flash column chromatography |
| TLC = | thin layer chromatography |
| TBAF = | tetrabutyl ammonium fluoride |
| DBU = | 1,8-diazabicyclo[5,4.0]undec-7-ene |
| EtOAc = | ethyl acetate |
| MTBE = | methyl t-butyl ether |

EXAMPLE 1

3-(1H-indol-3-yl)-4-[5-(4-methyl-piperazin-1-yl)-2-nitro-phenyl]-pyrrole-2,5-dione

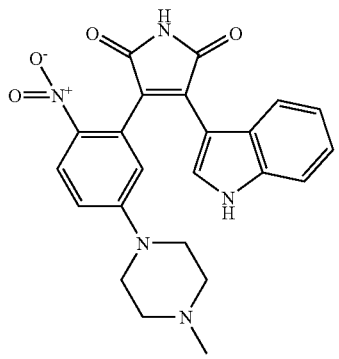

To a solution of 2-[5-(4-methyl-piperazin-1-yl)-2-nitro-phenyl]-acetamide (278 mg, 1.00 mmol) and (1H-indol-3-yl)-oxo-acetic acid methyl ester (366 mg, 1.80 mmol) in dry THF (8.0 mL) is added a solution of 1.0 M t-BuOK in THF (4.0 mL, 4.0 mmol) at 0° C. under argon. After stirring for 30 min at 0° C. and 1 h at RT, TLC indicates the complete consumption of the acetamide. The purple reaction mixture is partitioned between EtOAc (50 mL) and brine (50 mL), the layers are separated, and the aqueous layer is extracted with EtOAc (50 mL). The combined organic layers are dried over $Na_2SO_4$ and concentrated at reduced pressure. The crude product is purified by FCC (EtOAc/AcOH/$H_2O$ 7:1:1) to afford the title compound as its water soluble acetate salt. Orange solid. $^1$H NMR (DMSO-de, 400 MHz): δ 1.84 (s, 6H, $CH_3COO^-$), 1.97-2.15 (m, 4H), 2.03 (s, 3H), 2.95-3.21° (m, 4H), 6.51 (d, J=7.8 Hz, 1H), 6.54 (d, J=2.7 Hz, 1H), 6.73 (t, J=7.8 Hz, 1H), 7.01-7.07 (m, 2H), 7.41 (d, J=8.1 Hz, 1H), 8.00 (s, 1H), 8.13 (d, J=9.4 Hz, 1H), 10.8-11.4 (br, 1H), 11.95 (bs, 1H). $ES^+$-MS: 431 $[M+H]^+$.

Preparation of 2-[5-(4-Methyl-piperazin-1-yl)-2-nitro-phenyl]-acetamide

[5-(4-Methyl-piperazin-1-yl)-2-nitro-phenyl]-acetic acid ethyl ester (1.54 g, 5.01 mmol) is suspended in a 33% aqueous $NH_4OH$ solution (400 mL), and stirred for 3 days at RT. The volume is carefully reduced under vacuum until the title compound remains as a yellow solid, which is further dried under high vacuum. $ES^+$-MS: 279 $[M+H]^+$.

Preparation of [5-(4-Methyl-piperazin-1-yl)-2-nitro-phenyl]-acetic acid ethyl ester Under argon, a mixture of [5-bromo-2-nitro-phenyl]acetic acid ethyl ester (2.02 g, 7.00 mmol) and 1-methyl-piperazine (1.40 g, 14.0 mmol) is heated at 65° C. for 24 h. The reaction mixture is partitioned between $CH_2Cl_2$ (25 mL) and $H_2O$ (25 mL), and the aqueous layer is extracted with $CH_2Cl_2$ (2×25 mL). The combined organic layers are washed with brine (25 mL), dried over $Na_2SO_4$, and concentrated at reduced pressure. The crude product is purified by FCC($CH_2Cl_2$/MeOH 97.5:2.5) to afford the title compound as a yellow oil. $ES^+$-MS: 308 $[M+H]^+$.

Preparation of 5-Bromo-2-nitro-phenyl)-acetic acid ethyl ester

To a 1.0 M solution of t-BuOK in THF (60 mL, 60 mmol) is slowly added during 15 min a solution of 4-bromo-nitrobenzene (5.05 g, 25.0 mmol) and chloro-acetic acid ethyl ester (3.68 g, 30.0 mmol) in THF (30 mL) at 40° C. under argon. The deep blue reaction mixture is stirred for 1 h at 40° C. TLC analysis indicates the presence of some starting material at this time point. However, no further conversion of starting material is observed upon prolonged stirring. The reaction mixture is carefully quenched with a 2 M aqueous HCl solution (40 mL) and extracted with MTBE (2×100 mL). The combined organic phases are washed with $H_2O$ (100 mL), dried over $Na_2SO_4$, and concentrated at reduced pressure. The crude product is purified by FCC (cyclohexane/EtOAc 97:3) to yield the title compound as a colourless oil. $ES^+$-MS: 289 $[M+H]^+$.

EXAMPLE 2

3-[2-Amino-5-(4-methyl-piperazin-1-yl)-phenyl]-4-(1H-indol-3-yl)-pyrrole-2,5-dione

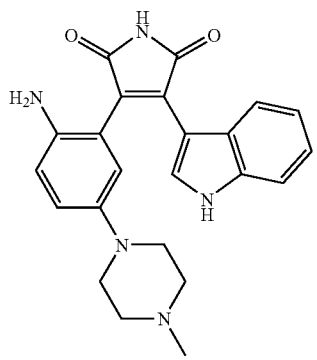

To a solution of 2-[2-amino-5-(4-methyl-piperazin-1-yl)-phenyl]-acetamide (124 mg, 0.50 mmol) and (1H-indol-3-yl)-oxo-acetic acid methyl ester (183 mg, 0.90 mmol) in dry THF (4.0 mL) is added a solution of 1.0 M t-BuOK in THF (2.0 mL, 2.0 mmol) at 0° C. under argon. After stirring for 30 min at 0° C. and 30 min at RT, TLC indicates the complete consumption of the acetamide. The dark red reaction mixture is partitioned between EtOAc (25 mL) and brine (25 mL), and the layers are separated. The pH of the aqueous layer is adjusted to 6 with a sat., aqueous $NH_4Cl$ solution. The aqueous layer is extracted with EtOAc (2×25 mL) and the combined organic layers are washed with brine (25 mL), dried over $Na_2SO_4$, and concentrated at reduced pressure. The crude product is purified by FCC (EtOAc/AcOH/$H_2O$ 5.5:1:1) to afford the title compound as its water soluble acetate salt. Red solid. $^1$H NMR (DMSO-$d_6$, 400 MHz): δ 1.70 (s, 9H, $CH_3COO^-$), 2.25 (s, 3H), 2.22-2.38 (m, 4H), 2.78-2.84 (m, 4H), 6.51 (d, J=8.7 Hz, 1H), 6.63 (d, J=2.8 Hz, 1H), 6.64-6.68 (m, 2H), 6.77 (dd, J=8.7 Hz, J=2.8 Hz, 1H), 6.97-7.02 (m, 1H), 7.35 (d, J=8.0 Hz, 1H), 7.90 (s, 1H), 11.91 (bs, 1H). $ES^+$-MS: 402 $[M+H]^+$.

Preparation of 2-[2-Amino-5-(4-methyl-piperazin-1-yl)-phenyl]-acetamide

To a solution of 2-[5-(4-methyl-piperazin-1-yl)-2-nitro-phenyl]-acetamide (468 mg, 1.68 mmol) in MeOH (8.0 mL) is added 10% Pd on charcoal (59 mg). The reaction mixture is stirred for 18 h under a hydrogen atmosphere (1 atm.), filtered through a microfilter (0.45 µM), and the filtrate concentrated at reduced pressure. The remaining brown oil is dissolved in MeOH (1 mL), MTBE (5 mL) is added, and the solvent is carefully removed at reduced pressure to afford the title compound as a beige powder. ES$^+$-MS: 249 [M+H]$^+$.

EXAMPLE 3

N-[2-[4-(1H-Indol-3-yl)-2,5-dioxo-2,5-dihydro-1H-pyrrol-3-yl]-4-(4-methyl-piperazin-1-yl)-phenyl]-acetamide

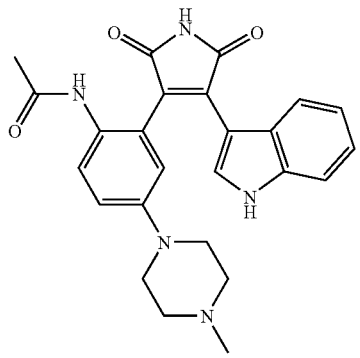

A

To a suspension of 2-[2-Acetylamino-5-(4-methyl-piperazin-1-yl)-phenyl]-acetamide (145 mg, 0.50 mmol) and (1H-indol-3-yl)-oxo-acetic acid methyl ester (183 mg, 0.90 mmol) in dry THF (6.0 mL) is added a solution of 1.0 M t-BuOK in THF (2.0 mL, 2.0 mmol) at 0° C. under argon. The resulting yellow suspension is stirred for 18 h at RT. The now dark red reaction mixture is partitioned between EtOAc (25 mL) and brine (25 mL), and the layers are separated. The pH of the aqueous layer is adjusted to 6 with a sat., aqueous NH$_4$Cl solution. The aqueous layer is extracted with EtOAc (2×25 mL) and the combined organic layers are washed with brine (25 mL), dried over Na$_2$SO$_4$, and concentrated at reduced pressure. The crude product is purified by FCC (EtOAc/AcOH/H$_2$O 5.5:1:1) to afford the title compound as its water soluble acetate salt. Orange solid. $^1$H NMR (DMSO-de, 400 MHz): δ 1.75 (s, 12H, CH$_3$COO), 2.16 (s, 3H), 2.31-2.38 (m, 4H), 2.92-2.99 (m, 4H), 6.61 (d, J=7.8 Hz, 1H), 6.66 (t, J=7.4 Hz, 1H), 6.75 (d, J=2.5 Hz, 1H), 6.92 (dd, J=9.0 Hz, J=2.7 Hz, 1H), 6.99 (t, J=7.5 Hz, 1H), 7.32 (d, J=8.1 Hz, 1H), 7.47 (d, J=8.9 Hz, 1H), 7.75 (s, 1H), 8.69 (s, 1H), 11.86 (bs, 1H). ES$^+$-MS: 444 [M+H]$^+$.

Preparation of 2-[2-Acetylamino-5-(4-methyl-piperazin-1-yl)-phenyl]-acetamide

[2-Acetylamino-5-(4-methyl-piperazin-1-yl)-phenyl]-acetic acid ethyl ester (450 mg, 1.41 mmol) is suspended in a 33% aqueous NH$_4$OH solution (200 mL), and stirred for 16 h at RT. The volume is carefully reduced under vacuum until the title compound remains as a brown solid, which is further dried under high vacuum. ES$^+$-MS: 291 [M+H]$^+$.

Preparation of [2-Acetylamino-5-(4-methyl-piperazin-1-yl)-phenyl]-acetic acid ethyl ester To a solution of [2-Amino-5-(4-methyl-piperazin-1-yl)-phenyl]-acetic acid ethyl ester (438 mg, 1.58 mmol) in CHCl$_3$ (8.0 mL) is added acetic acid anhydride (322 mg, 3.16 mmol) and triethyl amine (240 mg, 2.37 mmol) under argon. The resulting reaction mixture is stirred for 1 h at RT and 1 h at reflux. The reaction mixture is partitioned between CH$_2$Cl$_2$ (25 mL) and water (20 mL) and the layers are separated. The aqueous phase is extracted with CH$_2$Cl$_2$ (2×25 mL) and the combined organic layers are washed with water (2×25 mL), brine (25 mL), dried over Na$_2$SO$_4$ and concentrated at reduced pressure to afford a pale red solid. ES$^+$-MS: 320 [M+H]$^+$.

Preparation of [2-Amino-5-(4-methyl-piperazin-1-yl)-phenyl]-acetic acid ethyl ester To a solution of [5-(4-Methyl-piperazin-1-yl)-2-nitro-phenyl]-acetic acid ethyl ester (1.10 g, 3.58 mmol) in MeOH (25.0 mL) is added 10% Pd on charcoal (114 mg). The reaction mixture is stirred for 4 h under a hydrogen atmosphere (1 atm.), filtered through a microfilter (0.45 µM), and the filtrate concentrated at reduced pressure to afford the title compound as a red oil. ES$^+$-MS: 278 [M+H]$^+$.

By following the procedures of Examples 1, 2, and 3 or as described in WO 02/38561, but using the appropriate starting materials, the compounds of formula A wherein R$_a$, R$_b$, R$_3$ and R$_4$ are as indicated in Table 1 below, may be obtained.

TABLE 1

A

| Example | R$_3$ | R$_4$ | R$_a$ | R$_b$ | M.S. Data |
|---|---|---|---|---|---|
| 4. | 2-nitro | H | H | CH$_3$ | MH$^+$ 446 |
| 5. | 2-amino | H | H | CH$_3$ | MH$^+$ 416 |
| 6. | 2-acetamide | H | H | CH$_3$ | MH$^+$ 458 |
| 7. | 2-F | H | H | H | MH$^+$ 405 |
| 8. | 2-F | H | CH$_3$ | H | MH$^+$ 419 |
| 9. | 2-F | H | H | CH$_3$ | MH$^+$ 419 |
| 10. | 2-F | 4-F | H | H | MH$^+$ 423 |
| 11. | 2-F | 4-F | CH$_3$ | H | MH$^+$ 437 |
| 12. | 2-F | 4-F | H | CH$_3$ | MH$^+$ 437 |
| 13. | 2-Cl | 4-F | H | H | MH$^+$ 439 |
| 14. | 2-Cl | 4-F | H | CH$_3$ | MH$^+$ 453 |

The compounds of formula I in free form or in pharmaceutically acceptable salt form exhibit valuable pharmacological properties, e.g. inhibiting Protein Kinase C (PKC), e.g. PKC isoforms like α, β, δ, ε, η or θ activity, inhibiting T-cell activation and proliferation, e.g. by inhibiting production by T-cells or cytokines, e.g. IL-2, by inhibiting the proliferative response of T-cells to cytokines, e.g. IL-2, e.g. as indicated in in vitro and in vivo tests and are therefore indicated for therapy.

A. In vitro

1. Protein Kinase C Assay

The compounds of the invention are tested for their activity on different PKC isoforms according to the following method. Assay is performed in a white with clear bottom 384-well microtiterplate with non-binding surface. The reaction mixture (25 μl) contains 1.5 μM of a tridecapeptide acceptor substrate that mimics the pseudo substrate sequence of PKCα with the Ala→Ser replacement, 10 μM $^{33}$P-ATP, 10 mM $Mg(NO_3)_2$, 0.2 mM $CaCl_2$, PKC at a protein concentration varying from 25 to 400 ng/ml (depending on the isotype used), lipid vesicles (containing 30 mol % phosphatidylserine, 5 mol % DAG and 65 mol % phosphatidylcholine) at a final lipid concentration of 0.5 mM, in 20 mM Tris-HCl buffer pH 7.4+0.1% BSA. Incubation is performed for 60 min at room temperature. Reaction is stopped by adding 50 μl of stop mix (100 mM EDTA, 200 μM ATP, 0.1% Triton X-100, 0.375 mg/well streptavidin-coated SPA beads in phosphate buffered saline w/o Ca, Mg). After 10 min incubation at room temperature, the suspension is spun down for 10 min at 300 g. Incorporated radioactivity is measured in a Trilux counter for 1 min. $IC_{50}$ measurement is performed on a routine basis by incubating a serial dilution of inhibitor at concentrations ranging between 1-1000 μM. $IC_{50}$ values are calculated from the graph by curve fitting with XL fit® software.

2. Protein Kinase C θ Assay

Human recombinant PKCθ is used under the assay conditions as described above. In this assay, compounds of formula I inhibit PKC θ with an $IC_{50} \leq 1$ μM. For example, compound of Example 1 inhibits PKCθ with an $IC_{50}$ of 8.9 nM and compound of Example 4 inhibits PKCθ with an $IC_{50}$ of 10.2 nM.

3. Protein Kinase Cα Assay

Human recombinant PKCα was obtained from Oxford Biomedical Research and is used under the assay conditions as described under Section A.1 above. In this assay, compounds of formula I inhibit PKCα with an $IC_{50} \leq 1$ μM. For example, compound of Example 1 inhibits PKCα with an $IC_{50}$ of 2.6 nM compound of Example 4 inhibits PKCα with an $IC_{50}$ of 2.9 nM.

4. Protein Kinase Cβ1 Assay

Human recombinant PKCβ1 was obtained from Oxford Biomedical Research and is used under the assay conditions as described under Section A.1 above. In this assay, compounds of formula I inhibit PKCβ1 with an $IC_{50} \leq 1$ μM.

5. Protein Kinase Cδ Assay

Human recombinant PKCδ was obtained from Oxford Biomedical Research and is used under the assay conditions as described under Section A.1 above. In this assay, compounds of formula I inhibit PKCδ with an $IC_{50} \leq 1$ μM.

6. Protein Kinase Cε Assay

Human recombinant PKCε was obtained from Oxford Biomedical Research and is used under the assay conditions as described under Section A.1 above. In this assay, compounds of formula I inhibit PKCε with an $IC_{50} \leq 1$ μM.

7. Protein Kinase Cη Assay

Human recombinant PKCη was obtained from PanVera and is used under the assay conditions as described under Section A.1 above. In this assay, compounds of formula I inhibit PKCη with an $IC_{50} \leq 1$ μM.

8. CD28 Costimulation Assay

The assay is performed with Jurkat cells transfected with a human interleukin-2 promoter/reporter gene construct as described by Baumann G et al. in Transplant. Proc. 1992; 24:43-8, the β-galactosidase reporter gene being replaced by the luciferase gene (de Wet J., et al., Mol. Cell. Biol. 1987, 7(2), 725-737). Cells are stimulated by solid phase-coupled antibodies or phorbol myristate acetate (PMA) and the $Ca^{++}$ ionophore ionomycin as follows. For antibody-mediated stimulation Microlite TM1 microtiter plates (Dynatech) are coated with 3 μg/ml goat anti-mouse IgG Fc antibodies (Jackson) in 55 μl phosphate-buffered saline (PBS) per well for three hours at RT. Plates are blocked after removing the antibodies by incubation with 2% bovine serum albumin (BSA) in PBS (300 μl per well) for 2 hours at RT. After washing three times with 300 μl PBS per well, 10 ng/ml anti-T cell receptor antibodies (WT31, Becton & Dickinson) and 300 ng/ml anti-CD28 antibodies (15E8) in 50 μl 2% BSA/PBS are added as stimulating antibodies and incubated overnight at 4° C. Finally the plates are washed three times with 300 μl PBS per well. Seven three-fold serial dilutions of test compounds in duplicates in assay medium (RPMI 1640/10% fetal calf serum (FCS) containing 50 μM 2-mercaptoethanol, 100 units/ml penicillin and 100 μg/ml streptomycin) are prepared in separate plates, mixed with transfected Jurkat cells (clone K22 290_H23) and incubated for 30 minutes at 37° C. in 5% $CO_2$. 100 μl of this mixture containing $1 \times 10^5$ cells are then transferred to the antibody-coated assay plates. In parallel 100 μl are incubated with 40 ng/ml PMA and 2 μM ionomycin. After incubation for 5.5 hours at 37° C. in 5% $CO_2$, the level of luciferase is determined by bioluminescence measurement. The plates are centrifuged for 10 min at 500 g and the supernatant is removed by flicking. Lysis buffer containing 25 mM Tris-phosphate, pH 7.8, 2 mM DTT, 2 mM 1.2-diaminocyclohexane-N,N,N',N-tetraacetic acid, 10% (v/v) glycerol and 1% (v/v) Triton X-100 is added (20 μl per well). The plates are incubated at RT for 10 minutes under constant shaking. Luciferase activity is assessed with a bioluminescence reader (Labsystem, Helsinki, Finland) after automatic addition of 50 μl per well luciferase reaction buffer containing 20 mM Tricine, 1.07 mM $(MgCO_3)_4Mg(OH)_2 \times 5H_2O$, 2.67 mM $MgSO_4$, 0.1 mM EDTA, 33.3 mM DTT, 270 μM coenzyme A, 470 μM luciferin (Chemie Brunschwig AG), 530 μM ATP, pH 7.8. Lag time is 0.5 seconds, total measuring time is 1 or 2 seconds. Low control values are light units from anti-T cell receptor- or PMA-stimulated cells, high controls are from anti-T cell receptor/anti-CD28- or PMA/ionomycin-stimulated cells without any test sample. Low controls are subtracted from all values. The inhibition obtained in the presence of a test compound is calculated as percent inhibition of the high control. The concentration of test compounds resulting in 50% inhibition ($IC_{50}$) is determined from the dose-response curves. In this assay, compounds of formula I inhibit anti-T cell receptor/anti-CD28 and PMA/ionomycin stimulated Jurkat cells with an $IC_{50} \leq 1$ μM.

For example, compound of Example 1 has an $IC_{50}$ of 25.5 nM and compound of Example 4 has an $IC_{50}$ of 17.0 nM.

9. Allogeneic Mixed Lymphocyte Reaction (MLR)

The two-way MLR is performed according to standard procedures (J. Immunol. Methods, 1973, 2, 279 and Meo T. et al., Immunological Methods, New York, Academic Press, 1979, 227-39). Briefly, spleen cells from CBA and BALB/c mice ($1.6 \times 10^5$ cells from each strain per well in flat bottom tissue culture microtiter plates, $3.2 \times 10^5$ in total) are incubated in RPMI medium containing 10% FCS, 100 U/ml penicillin, 100 μg/ml streptomycin (Gibco BRL, Basel, Switzerland), 50 μM 2-mercaptoethanol (Fluka, Buchs, Switzerland) and serially diluted compounds. Seven three-fold dilution steps in duplicates per test compound are performed. After four days of incubation 1 μCi $^3$H-thymidine is added. Cells are harvested after an additional five-hour incubation period, and incorporated $^3$H-thymidine is determined according to standard procedures. Background values (low control) of the MLR are the experimental groups to the weight difference between the corresponding lymph nodes from a group of animals left untreated with a test compound.

The compounds of formula I are, therefore, useful in the treatment and/or prevention of diseases or disorders mediated by T lymphocytes and/or PKC, e.g. acute or chronic rejection of organ or tissue allo- or xenografts, graft versus host diseases, atherosclerosis, vascular occlusion due to vascular injury such as angioplasty, restenosis, obesity, syndrome X, impaired glucose tolerance, polycystic ovary syndrome, hypertension, heart failure, chronic obstructive pulmonary disease, CNS diseases such as Alzheimer disease or amyotrophic lateral sclerosis, cancer, infectious diseases such as AIDS, septic shock or adult respiratory distress syndrome, ischemia/reperfusion injury e.g. myocardial infarction, stroke, gut ischemia, renal failure or hemorrhage shock, or traumatic shock, e.g. traumatic brain injury. The compounds of formula I are also useful in the treatment and/or prevention of T-cell mediated acute or chronic inflammatory diseases or disorders or autoimmune diseases e.g. rheumatoid arthritis, osteoarthritis, systemic lupus erythematosus, Hashimoto's thyroidis, multiple sclerosis, myasthenia gravis, diabetes type I or II and the disorders associated therewith, respiratory diseases such as asthma or inflammatory lung injury, inflammatory liver injury, inflammatory glomerular injury, cutaneous manifestations of immunologically-mediated disorders or illnesses, inflammatory and hyperproliferative skin diseases (such as psoriasis, atopic dermatitis, allergic contact dermatitis, irritant contact dermatitis and further eczematous dermatitses, seborrhoeic dermatitis), inflammatory eye diseases, e.g. Sjoegren's syndrome, keratoconjunctivitis or uveitis, inflammatory bowel disease, Crohn's disease or ulcerative colitis. For the above uses the required dosage will of course vary depending on the mode of administration, the particular condition to be treated and the effect desired. In general, satisfactory results are indicated to be obtained systemically at daily dosages of from about 0.1 to about 100 mg/kg body weight. An indicated daily dosage in the larger mammal, e.g. humans, is in the range from about 0.5 mg to about 2000 mg, conveniently administered, for example, in divided doses up to four times a day or in retard form.

The compounds of formula I may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, or in a nasal or a suppository form. Pharmaceutical compositions comprising a compound of formula I in free form or in pharmaceutically acceptable salt form in association with at least one pharmaceutical acceptable carrier or diluent may be manufactured in proliferation of BALB/c cells alone. Low controls are subtracted from all values. High controls without any sample are taken as 100% proliferation. Percent inhibition by the samples is calculated, and the concentrations required for 50% inhibition ($IC_{50}$ values) are determined. For example, compound of Example 1 has an $IC_{50}$ of 17.5 nM and compound of Example 4 has an $IC_{50}$ of 24.0 nM.

B. In Vivo

Rat Heart Transplantation

The strain combination used: Male Lewis ($RT^1$ haplotype) and BN ($RT^1$ haplotype). The animals are anaesthetised using inhalational isofluorane. Following heparinisation of the donor rat through the abdominal inferior vena cava with simultaneous exsanguination via the aorta, the chest is opened and the heart rapidly cooled. The aorta is ligated and divided distal to the first branch and the brachiocephalic trunk is divided at the first bifurcation. The left pulmonary artery is ligated and divided and the right side divided but left open. All other vessels are dissected free, ligated and divided and the donor heart is removed into iced saline.

The recipient is prepared by dissection and cross-clamping of the infra-renal abdominal aorta and vena cava. The graft is implanted with end-to-side anastomoses, using 10/0 monofilament suture, between the donor brachiocephalic trunk and the recipient aorta and the donor right pulmonary artery to the recipient vena cava. The clamps are removed, the graft tethered retroabdominally, the abdominal contents washed with warm saline and the animal is closed and allowed to recover under a heating lamp. Graft survival is monitored by daily palpation of the beating donor heart through the abdominal wall. Rejection is considered to be complete when heart beat stops. Increases of graft survival are obtained in animals treated with a compound of formula I administered orally at a daily dose of 1 to 30 mg/kg bid.

Graft v. Host Model

Spleen cells ($2\times10^7$) from Wistar/F rats are injected subcutaneously into the right hind footpad of (Wistar/F×Fischer 344)$F_1$ hybrid rats. The left footpad is left untreated. The animals are treated with the test compounds on 4 consecutive days (0-3). The popliteal lymph nodes are removed on day 7, and the weight differences between two corresponding lymph nodes are determined. The results are expressed as the inhibition of lymph node enlargement (given in percent) comparing the lymph node weight differences in the conventional manner by mixing with a pharmaceutically acceptable carrier or diluent. Unit dosage forms for oral administration contain, for example, from about 0.1 mg to about 500 mg of active substance.

Topical administration is e.g. to the skin. A further form of topical administration is to the eye.

The compounds of formula I may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by T lymphocytes and/or PKC or G SK-3β, e.g. such as indicated above, in a subject in need of such treatment, which method comprises administering to said subject an effective amount of a compound of formula I or a pharmaceutically acceptable salt thereof;

1.2 A method for preventing or treating acute or chronic transplant rejection or T-cell mediated inflammatory or autoimmune diseases, e.g. as indicated above, in a subject in need of such treatment, which method comprises administering to said subject an effective amount of a compound of formula I or a pharmaceutically acceptable salt thereof;

2. A compound of formula I, in free form or in a pharmaceutically acceptable salt form for use as a pharmaceutical, e.g. in any of the methods as indicated under 1.1 and 1.2 above.

3. A pharmaceutical composition, e.g. for use in any of the methods as in 1.1 and 1.2 above comprising a compound of formula I in free form or pharmaceutically acceptable salt form in association with a pharmaceutically acceptable diluent or carrier therefor.

4. A compound of formula I or a pharmaceutically acceptable salt thereof for use in the preparation of a pharmaceutical composition for use in any of the method as in 1.1 and 1.2 above.

Compounds of formula I may be administered as the sole active ingredient or together with other drugs in immunomodulating regimens or other anti-inflammatory agents e.g. for the treatment or prevention of allo- or xenograft acute or chronic rejection or inflammatory or autoimmune disorders. For example, they may be used in combination with cyclosporines, or ascomycines or their immunosuppressive analogs or derivatives, e.g. cyclosporin A, ISA Tx247, FK-506, ABT-281, ASM 981; an mTOR inhibitor, e.g. rapamycin, 400-(2-hydroxy)ethyl-rapamycin, CCI779, ABT578 or a rapalog, e.g. AP23573 etc.; corticosteroids; cyclophosphamide; azathioprine; methotrexate; a S1P receptor agonist e.g. FTY720 or an analogue thereof; leflunomide or analogs thereof; mizoribine; mycophenolic acid or a salt thereof, e.g. sodium salt; mycophenolate mofetil; 15-deoxyspergualin or analogs thereof; immunosuppressive monoclonal antibodies, e.g., monoclonal antibodies to leukocyte receptors, e.g., MHC, CD2, CD3, CD4, CD11a/CD18, CD7, CD25, CD 27, B7, CD40, CD45, CD58, CD 137, ICOS, CD150 (SLAM), OX40, 4-1BB or their ligands, e.g. CD154; or other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y, or other adhesion molecule inhibitors, e.g. mAbs or low molecular weight inhibitors including LFA-1 antagonists, Selectin antagonists and VLA-4 antagonists. Compounds of formula I may also be administered together with an antiproliferative drug, e.g. a chemotherapeutic drug, e.g. in cancer treatment, or with an anti-diabetic drug, an insulin secretagogue, insulin secretion enhancer or an insulin sensitizer, in diabetes therapy, In accordance with the foregoing the present invention provides in a yet further aspect:

5. A method as defined above comprising co-administration, e.g. concomitantly or in sequence, of a therapeutically effective amount of an inhibitor of GSK-3β, PKC or of T-cell activation and proliferation, e.g. a compound of formula I in free form or in pharmaceutically acceptable salt form, and a second drug substance, said second drug substance being an immunosuppressant, immunomodulatory, anti-inflammatory, antiproliferative or anti-diabetic drug, e.g. as indicated above.

6. A therapeutic combination, e.g. a kit, comprising a) an inhibitor of GSK-3β, PKC or of T-cell activation and proliferation, e.g. a compound of formula I in free form or in pharmaceutically acceptable salt form, and b) at least one second agent selected from an immunosuppressant, immunomodulatory, anti-inflammatory, antiproliferative and anti-diabetic drug. Component a) and component b) may be used concomitantly or in sequence. The kit may comprise instructions for its administration.

Where an inhibitor of GSK-3β, PKC or of T-cell activation and proliferation, e.g. a compound of formula I, is administered in conjunction with other immunosuppressive/immunomodulatory, anti-inflammatory, antiproliferative or anti-diabetic therapy, e.g. for preventing or treating acute or chronic graft rejection or inflammatory or autoimmune disorders as hereinabove specified, dosages of the co-administered immunosuppressant, immunomodulatory, anti-inflammatory, antiproliferative or antidiabetic compound will of course vary depending on the type of co-drug employed, e.g. whether it is a steroid or a cyclosporine, on the specific drug employed, on the condition being treated and so forth.

The invention claimed is:

1. A compound of formula I:

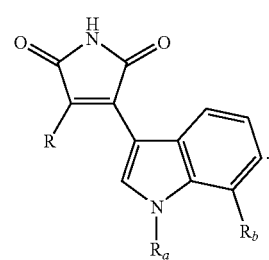

I wherein:
$R_a$ is H or methyl;
$R_b$ is H, ethyl or methyl; and
R is a radical of formula (a)

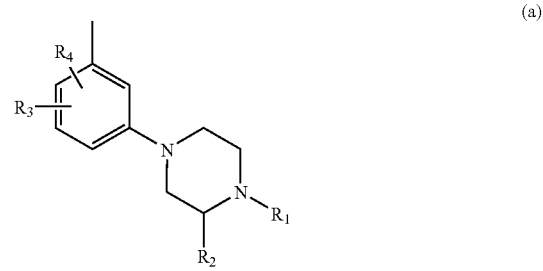

(a)

wherein $R_1$ is methyl and $R_2$ is H or methyl;
$R_3$ is F or nitro and is attached at position 2; and
$R_4$ is H or F and is attached at position 4;
or a pharmaceutically-acceptable salt thereof.

2. The compound according to claim 1 selected from
3-(1H-indol-3-yl)-4-[5-(4-methyl-piperazin-1-yl)-2-nitro-phenyl]-pyrrole-2,5-dione;
3-(7-methyl-1H-indol-3-yl)-4-[5-(4-methyl-piperazin-1-yl)-2-nitro-phenyl]-pyrrole-2,5-dione;
3-[2-fluoro-5-(4-methyl-piperazin-1-yl)-phenyl]-4-(1H-indol-3-yl)-pyrrole-2,5-dione;
3-[2-fluoro-5-(4-methyl-piperazin-1-yl)-phenyl]-4-(1-methyl-1H-indol-3-yl)-pyrrole-2,5-dione;
3-[2-fluoro-5-(4-methyl-piperazin-1-yl)-phenyl]-4-(7-methyl-1H-indol-3-yl)-pyrrole-2,5-dione;
3-[2,4-difluoro-5-(4-methyl-piperazin-1-yl)-phenyl]-4-(1H-indol-3-yl)-pyrrole-2,5-dione; and
3-[2,4-difluoro-5-(4-methyl-piperazin-1-yl)-phenyl]-4-(1-methyl-1H-indol-3-yl)-pyrrole-2,5-dione;
or a pharmaceutically-acceptable salt thereof.

3. A pharmaceutical composition comprising a compound according to claim 1, in free form or in pharmaceutically-acceptable salt form, in association with a pharmaceutically-acceptable diluent or carrier thereof.

4. A pharmaceutical combination comprising a compound according to claim 1, in free form or in a pharmaceutically acceptable salt form, and a further agent selected from immunosuppressant, immunomodulatory, anti-inflammatory, chemotherapeutic, antiproliferative and anti-diabetic agents.

5. A process for the production of the compound of formula I according to claim 1, which process comprises reacting a compound of formula (II):

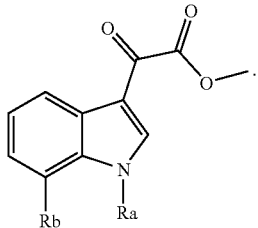
(II)

with a compound of formula (III):

R—CH$_2$—CO—NH$_2$   (III), wherein R is as defined in claim 1;

and, optionally, converting the resulting compound of formula I obtained in free form to a salt form or vice versa, as desired.

wherein R$_a$ and R$_b$ are as defined in claim 1,

* * * * *